United States Patent
Kristen et al.

(10) Patent No.: US 6,936,563 B2
(45) Date of Patent: Aug. 30, 2005

(54) COORDINATION COMPOUNDS AND THEIR USE FOR THE POLYMERIZATION OF OLEFINS

(75) Inventors: Marc Oliver Kristen, Limburgerhof (DE); Benno Bildstein, Innsbruck (AT); Alexander Krajete, Salzburg (AT)

(73) Assignee: BASF Aktiengesellschaft, Ludwigshafen (DE)

( * ) Notice: Subject to any disclaimer, the term of this patent is extended or adjusted under 35 U.S.C. 154(b) by 197 days.

(21) Appl. No.: 10/467,792
(22) PCT Filed: Feb. 7, 2002
(86) PCT No.: PCT/EP02/01256
§ 371 (c)(1), (2), (4) Date: Aug. 12, 2003
(87) PCT Pub. No.: WO02/064602
PCT Pub. Date: Aug. 22, 2002

(65) Prior Publication Data
US 2004/0030069 A1 Feb. 12, 2004

(30) Foreign Application Priority Data
Feb. 13, 2001 (DE) .......................... 101 07 043

(51) Int. Cl.$^7$ .............................. B01J 31/38; C08F 4/72
(52) U.S. Cl. .................... 502/117; 502/155; 502/167; 526/127; 526/128; 526/161; 526/171
(58) Field of Search ................................ 502/117, 155, 502/167; 526/161, 171, 127, 128

(56) References Cited

U.S. PATENT DOCUMENTS 3,997,471 A * 12/1976 Ofstead ...................... 502/117

FOREIGN PATENT DOCUMENTS

| EP | 0 874 005 | 10/1998 |
| WO | 96/23010 | 8/1996 |
| WO | 98/27124 | 6/1998 |

OTHER PUBLICATIONS

H.-H. Brintzinger et al. Angew Chem., vol. 107, pp. 1255–1281 1995.
G.J.P. Britovsek et al. Angew Chem. Int. Ed. Engl., vol. 38, pp. 429–447 1999.
Bei et al. Organometallics, vol. 16, pp. 3282–3300 1997.
T. Tsukahara et al. Organometallics, vol. 16, pp. 3303–3313 1997.
I. Kim et al. Organometallics, vol. 16, pp. 3314–3323 1997.

* cited by examiner

*Primary Examiner*—Robert D. Harlan
(74) *Attorney, Agent, or Firm*—Oblon, Spivak, McClelland, Maier & Neustadt, P.C.

(57) ABSTRACT

The invention relates to coordination compounds of the general formulae (Ia) to (Ib), wherein M=Ti, Zr, Hf, V, Nb or Ta. The invention also relates to a method for producing the metal complexes and to the use of the complexes so obtained for the polymerization and copolymerization of olefins. For example in suspension polymerization methods, gas phase polymerization methods and bulk polymerization methods

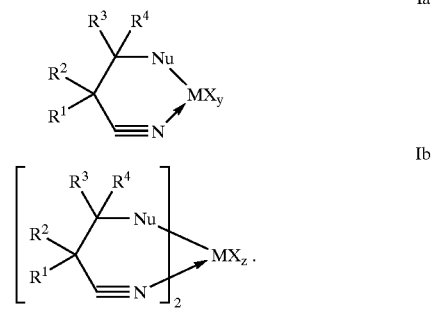

13 Claims, No Drawings

COORDINATION COMPOUNDS AND THEIR USE FOR THE POLYMERIZATION OF OLEFINS

The present invention relates to complexes of the formulae I a and I b,

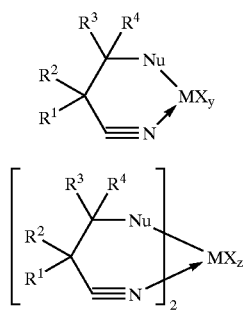

where the variables are defined as follows:
M is selected from among Ti, Zr, Hf, V, Nb and Ta;
y corresponds to the oxidation state of M minus 1;
z corresponds to the oxidation state of M minus 2;
Nu is selected from among O, S and N—$R^5$;
X are identical or different and are selected from among halogen, $C_1$–$C_8$-alkyl, $C_3$–$C_{12}$-cycloalkyl, $C_7$–$C_{13}$-aralkyl and $C_6$–$C_{14}$-aryl,
$R^1$ to $R^5$ are identical or different and are selected from among hydrogen,
  $C_1$–$C_{18}$-alkyl, substituted or unsubstituted,
  $C_2$–$C_{18}$-alkenyl, substituted or unsubstituted, having from one to 4 isolated or conjugated double bonds;
  $C_3$–$C_{12}$-cycloalkyl, substituted or unsubstituted,
  $C_7$–$C_{13}$-aralkyl,
  $C_6$–$C_{14}$-aryl, unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy, substituted or unsubstituted,
    $C_6$–$C_{14}$-aryloxy,
    $SiR^6R^7R^8$ and O—$SiR^6R^7R^8$;
  five- and six-membered nitrogen-containing heteroaryl radicals, unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^6R^7R^8$ and O—$SiR^6R^7R^8$;
where adjacent radicals $R^1$ to $R^5$ may be joined to one another to form a 5- to 12-membered ring which may in turn bear substituents selected from among $C_1$–$C_8$-alkyl, substituted or unsubstituted, $C_2$–$C_8$-alkenyl, substituted or unsubstituted and having from one to 4 isolated or conjugated double bonds, $C_3$–$C_{12}$-cycloalkyl, substituted or unsubstituted, $C_7$–$C_{13}$-aralkyl and $C_6$–$C_{14}$-aryl;

$R^6$ to $R^8$ are identical or different and are selected from among hydrogen, $C_1$–$C_8$-alkyl, $C_3$–$C_{12}$-cycloalkyl, $C_7$–$C_{13}$-aralkyl and $C_6$–$C_{14}$-aryl.

The present invention also relates to a process for the polymerization of olefins using complexes of the formulae I a and I b.

Polymers and copolymers of olefins are of great economic importance because the monomers are readily available in large quantities and because the polymers can be varied within a wide range by variation of the method of preparation or the processing parameters. The catalyst used is of particular significance in the process for preparing the polymers. Apart from Ziegler-Natta catalysts, various single-site catalysts are of increasing importance. In the latter, central atoms which have been examined in some detail include not only Zr as in, for example, metallocene catalysts (H.-H. Brintzinger et al., *Angew. Chem.* 1995, 107, 1255) but also Ni or Pd (WO 96/23010) or Fe and Co (e.g. WO 98/27124). The complexes of Ni, Pd, Fe and Co are also referred to as complexes of late transition metals.

Metallocene catalysts have disadvantages for industrial use. The most frequently employed metallocenes, namely zirconocenes and hafnocenes, are sensitive to hydrolysis. In addition, most metallocenes are sensitive to many catalyst poisons such as alcohols, ethers and Co, which makes it necessary for the monomers to be carefully purified.

While Ni and Pd complexes (WO 96/23010) catalyze the formation of highly branched polymers which are of little commercial interest, the use of Fe or Co complexes leads to formation of highly linear polyethylene containing very low proportions of comonomer.

EP-A 0 874 005 discloses further polymerization-active complexes. These complexes are preferably Ti complexes with salicylaldimine ligands. These, too, bear phenyl substituents or substituted phenyl substituents on the aldimine nitrogen (pages 18–23), or else the aldimine nitrogen is incorporated in a 6-membered ring (pages 31–32). However, they generally produce low molecular weight polyethylenes which are not very suitable as materials. Furthermore, all the ligands disclosed in EP-A 0 874 005 have the oxygen atom as part of a phenolic system, which restricts the choice of readily available starting materials.

As G. J. P. Britovsek et al. show in Angew. Chem. 1999, 111, 448 and Angew. Chem. Int. Ed. Engl. 1999, 38, 428, the search for very versatile polymerization-active complexes continues to be of importance because of the great commercial importance of polyolefins. Particular attention has been attracted by complexes of the early transition metals with bidentate ligands, for example complexes of the formula A,

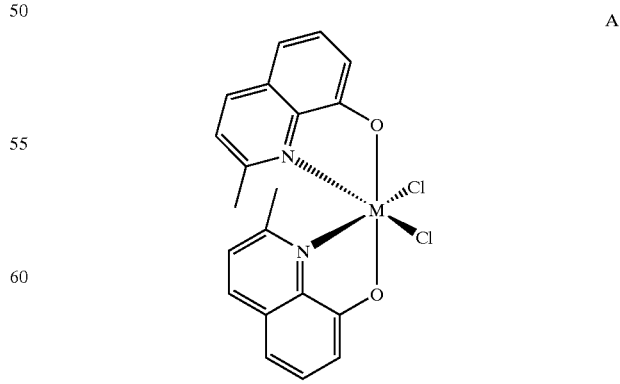

which have been examined by X. Bei et al. in Organometallics 1997, 16, 3282. However, the activities of the complexes in which M=Ti or Zr in the polymerization of ethylene were too low for the complexes to be of commercial interest. T. Tsukahara et al. in Organometallics 1997, 16, 3303 and I. Kim et al. in Organometallics 1997, 16, 3314 have examined β-hydroxypyridyl complexes of the formula B

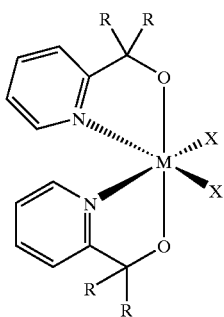

and their activity in the polymerization of ethylene. If, for example, R are each selected from among $CH_3$ and $CF_3$ and X is benzyl or neopentyl, only an extremely low polymerization activity, if any, opposite ethylene could be observed when the complex was activated with trispentafluorophenylborane. On the other hand, if R=para-tert-butylphenyl and X=benzyl, a low activity was observed, but this was too low for commercial purposes. In addition, the polymers prepared in this way had a molecular weight $M_n$ of 6200 g which is too low for materials.

It is known from U.S. Pat. No. 3,997,471 that complexes formed in situ from β-hydroxynitriles and $WCl_6$ or their homologous molybdenum analogues are able, after activation by various aluminum alkyl compounds such as ethylaluminum dichloride or diethylaluminum chloride, to polymerize cyclic olefins with opening of the ring.

It is therefore an object of the invention
to provide new complexes which are suitable for the polymerization of olefins to give high molecular weight polyolefins;
to provide a process for preparing the complexes of the present invention;
to provide a process for the polymerization or copolymerization of olefins using the complexes of the present invention;
to provide supported catalysts for the polymerization of olefins and a process for preparing the supported catalysts of the present invention using the complexes of the present invention; and
to polymerize and copolymerize olefins using the supported catalysts of the present invention.

We have found that this object is achieved by means of complexes having the structures of the formulae I a and I b defined at the outset.

In formula I, the variables are defined as follows:
Nu is selected from among O, S and N—$R^5$, with oxygen being preferred;
M is selected from among Ti, Zr, Hf, V, Nb and Ta in the oxidation states from +3 to +5; preferably Ti or Zr and particularly preferably Zr;
y corresponds to the oxidation state of M minus 1,
z corresponds to the oxidation state of M minus 2, where M can be a metal in the highest oxidation state but does not have to be;
X are identical or different and are selected from among halogen, such as fluorine, chlorine, bromine and iodine, with preference being given to chlorine or bromine and particular preference being given to chlorine;

$C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl; and $C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

X is preferably halogen.
$R^1$ to $R^5$ are identical or different and are selected from among
hydrogen,
$C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: β-cyanoethyl, monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_8$-alkenyl groups are: isopropenyl, 1-isoprenyl, α-styryl, β-styryl, 1-cis-1,2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl substituted by one or more identical or different substituents selected from among $C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl, preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_{18}$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_8$-alkenyl groups are: isopropenyl, 1-isoprenyl, α-styryl, β-styryl, 1-cis-1,2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^6R^7R^8$, where $R^6$ to $R^8$ are selected independently from among hydrogen, $C_1$–$C_8$-alkyl groups, benzyl radicals and $C_6$–$C_{14}$-aryl groups; with preference being given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups and particular preference being given to the trimethylsilyl group and the tert-butyldimethylsilyl group;

silyloxy groups $OSiR^6R^7R^8$, where $R^6$ to $R^8$ are selected independently from among hydrogen, $C_1$–$C_8$-alkyl groups, benzyl radicals and $C_6$–$C_{14}$-aryl groups; with preference being given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups and particular preference being given to the trimethylsilyloxy group and the tert-butyldimethylsilyloxy group;

five and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl substituted by one or more identical or different substituents selected from among $C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl, preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_8$-alkenyl groups are: isopropenyl, 1-isoprenyl, α-styryl, β-styryl, 1-cis-1,2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^6R^7R^8$, where $R^6$ to $R^8$ are selected independently from among hydrogen, $C_1$–$C_8$-alkyl groups, benzyl radicals and $C_6$–$C_{14}$-aryl groups; with preference being given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups and particular preference being given to the trimethylsilyl group and the tert-butyldimethylsilyl group;

silyloxy groups $OSiR^6R^7R^8$, where $R^6$ to $R^8$ are selected independently from among hydrogen, $C_1$–$C_8$-alkyl groups, benzyl radicals and $C_6$–$C_{14}$-aryl groups; with preference being given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups and particular preference being given to the trimethylsilyloxy group and the tert-butyldimethylsilyloxy group.

In a particularly preferred embodiment, at least one of the radicals $R^1$ to $R^4$ is different from hydrogen. In a particularly preferred embodiment, $R^2$ or $R^3$ is different from hydrogen.

In a particular embodiment, adjacent radicals $R^1$ to $R^5$ of the complexes of the formulae I a and I b may be joined to one another to form a 5- to 12-membered ring. For example, $R^1$ and $R^2$ may together be: —(CH$_2$)$_3$—(trimethylene), —(CH$_2$)$_4$—(tetramethylene), —(CH$_2$)$_5$—(pentamethylene), —(CH$_2$)$_6$—(hexamethylene), —CH$_2$—CH=CH—, —CH$_2$—CH=CH—CH$_2$—, —CH=CH—CH=CH—, —O—CH$_2$—O—, —O—CHMe-O—, —O—CH—(C$_6$H$_5$)—O—, —O—CH$_2$—CH$_2$—O—, —O—CMe$_2$—O—, —NMe-CH$_2$—CH$_2$—NMe—, —NMe-CH$_2$—NMe— or —O—SiMe$_2$—O— where Me=CH$_3$.

The complexes required for the process of the present invention are obtainable from commercially available reagents in only a few steps.

The synthesis of the novel complexes of the formula I generally starts out from a ligand of the formula II,

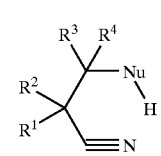

where the variables are as defined above.

The ligands of the formula II are firstly deprotonated by means of a base and subsequently reacted with metal compounds of the formula $MX_{y+1}$.

Bases which can be used are the metal alkyls customary in organometallic chemistry, for example methyllithium, ethyllithium, n-butyllithium, sec-butyllithium, tert-butyllithium or hexyllithium, also Grignard compounds such as ethylmagnesium bromide, also lithium amide, sodium amide, potassium amide, potassium hydride or lithium diisopropylamide ("LDA"). Solvents which have been found to be useful are high-boiling solvents such as toluene, ortho-xylene, meta-xylene, para-xylene, ethylbenzene or mixtures of these, also acyclic or cyclic ethers such as 1,2-dimethoxyethane, tetrahydrofuran or diethyl ether.

This deprotonation is generally complete after a few hours; it is appropriate to employ a reaction time of from 2 to 10 hours, preferably from 3 to 5 hours. The temperature conditions are generally not critical; temperatures of from −90° C. to −20° C. are preferred for the deprotonation.

The deprotonated ligand and the metal compound of the formula $MX_{y+1}$ are subsequently reacted with one another.

$MX_{y+1}$ can optionally be stabilized by additional uncharged ligands. Possible uncharged ligands are the customary ligands of coordination chemistry, for example cyclic and acyclic ethers, amines, diamines, nitriles, isonitriles or phosphines. Particular preference is given to diethyl ether, tetrahydrofuran, 1,2-dimethoxyethane, tetramethylethylenediamine, acetonitrile or triphenylphosphane.

The conditions for the reaction are not critical per se; it is usual to mix the deprotonated ligand II and $MX_{y+1}$ with one another in a suitable solvent such as benzene, toluene, ethylbenzene, ortho-xylene, meta-xylene or para-xylene, chlorobenzene, cyclohexane, methylene chloride or a mixture of these. The temperature can be in the range from −100° C. to +150° C., preferably from −78° C. to +100° C. The reaction temperature should not be less than the melting point of the solvent; temperatures above the boiling point of the solvent concerned can be achieved in an autoclave. It is important that the reaction is carried out in the absence of oxygen and moisture.

The molar ratio of ligand to M can be in the range from 5:1 to 1:5. However, since the ligands of the formula II are more difficult to obtain than the metal compounds, molar ratios of ligand:M in the range from 1:1 to 1:3 are preferred. Particular preference is given to stoichiometric amounts.

However, if compounds of the formula I b are to be obtained, molar ratios of ligand:M of from 2:1 to 4:1 are preferred.

The novel complexes of the formulae I a and I b can be purified by the methods customary in organometallic chemistry, with particular preference being given to crystallization and precipitation. Filtration via filter aids such as Celite® is also useful.

The preparation of the ligands of the formula II is described, for example, in U.S. Pat. No. 3,997,471. The preparation is advantageously carried out by deprotonation of a nitrile of the formula III,

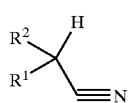

III which bears an acidic α-H atom and subsequent reaction with an electrophilic compound of the formula IV,

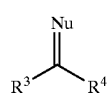

IV where the variables in the compounds III and IV are as defined above.

Bases which can be used are the metal alkyls customary in organometallic chemistry, for example methyllithium, ethyllithium, n-butyllithium, sec-butyllithium, tert-butyllithium or hexyllithium, also Grignard compounds such as ethylmagnesium bromide, also lithium amide, sodium amide, potassium amide, potassium hydride or lithium diisopropylamide ("LDA"). Solvents which have been found to be useful are, for example, toluene, ortho-xylene, meta-xylene, para-xylene, ethylbenzene or mixtures of these, also acyclic or cyclic ethers such as 1,2-dimethoxyethane, tetrahydrofuran or diethyl ether.

This deprotonation is generally complete after from some minutes to a few hours; it is appropriate to employ a reaction time of from 30 minutes to 10 hours, preferably from 1 to 5 hours. The temperature conditions are generally not critical; temperatures of from −90° C. to +30° C.

The deprotonated nitrile III and the electrophilic compound IV are subsequently reacted with one another.

The conditions for the reaction are not critical per se; it is usual to mix the deprotonated nitrile III and the electrophilic compound IV with one another in a suitable solvent such as benzene, toluene, ethylbenzene, ortho-xylene, meta-xylene or para-xylene, chlorobenzene, cyclohexane, methylene chloride or a mixture of these. The temperature can be in the range from −100° C. to +150° C., preferably from −78° C. to +100° C. The reaction temperature should not be less than the melting point of the solvent; temperatures above the boiling point of the solvent concerned can be achieved in an autoclave. It is important that the reaction is carried out in the absence of oxygen and moisture.

The molar ratio of III to IV can be in the range from 5:1 to 1:5. Preference is given to molar ratios of III:IV in the range from 3:1 to 1:3 and particular preference is given to stoichiometric amounts.

It has been found that the novel complexes of the formulae I a and I b are suitable for polymerizing olefins. They are particularly useful for polymerizing and copolymerizing ethylene and propylene to form high molecular weight polymers. Complexes of the formula I b are chiral and can produce isotactic polypropylene in the polymerization of propylene.

For the novel complexes of the formulae I a and I b to be catalytically active, they have to be activated. Suitable activators are selected aluminum and boron compounds bearing electron-withdrawing radicals (e.g. trispentafluorophenylborane, trispentafluorophenylaluminum, N,N-dimethylanilinium tetrakispentafluorophenylborate, tri-n-butylaimonium tetrakispentafluorophenylborate, N,N-dimethylanilinium tetrakis(3,5-bisperfluoromethyl)phenylborate, tri-n-butylarmonium tetrakis(3,5-bisperfluoromethyl)phenylborate and tritylium tetrakispentafluorophenylborate). Preference is given to dimethylanilinium tetrakispentafluorophenylborate, tritylium tetrakispentafluorophenylborate and trispentafluorophenylborane.

If boron or aluminum compounds are used as activators for the novel complexes of the formulae I a and I b, they are generally used in a molar ratio of from 1:10 to 10:1, based on M. They are preferably used in a ratio of from 1:2 to 5:1 and particularly preferably in stoichiometric amounts.

Another suitable class of activators consists of aluminoxanes. The structure of the aluminoxanes is not known precisely. They are products which are obtained by careful partial hydrolysis of aluminum alkyls (cf. DE-A 30 07 725). These products are not in the form of pure chemical compounds, but as mixtures of open-chain and cyclic structures of the types V a and V b. These mixtures are presumably in dynamic equilibrium.

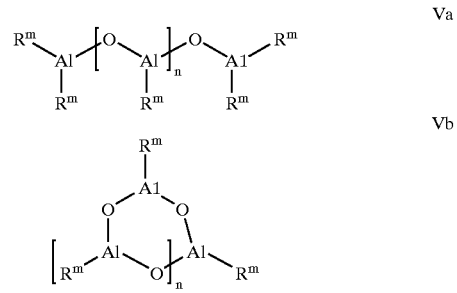

In the formulae V a and V b, the radicals Rm are each, independently of one another, $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl, preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

$C_2$–$C_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl, preferably cyclopentyl, cyclohexyl or cycloheptyl;

$C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, or $C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl or 2-naphthyl, particularly preferably phenyl; and n is an integer from 0 to 40, preferably from 1 to 25 and particularly preferably from 2 to 22.

Cage-like structures for aluminoxanes are also discussed in the literature (Y. Koide, S. G. Bott, A. R. Barron Organometallics 1996, 15, 2213–26; A. R. Barron Macromol. Symp. 1995, 97, 15–25). Regardless of the actual structure of the aluminoxanes, they are suitable as activators for the novel metal complexes of the formulae I a and I b.

Mixtures of various aluminoxanes are particularly preferred activators in cases when the polymerization is carried out in a solution in a paraffin, for example n-heptane or isododecane. A particularly preferred mixture is the CoMAO available commercially from Witco GmbH, which has the formula $[(CH_3)_{0.9}(iso-C_4H_9)_{0.1}AlO]_n$.

To activate the complexes of the formulae I a and I b by means of aluminoxanes, an excess of aluminoxane, based on M, is generally necessary. Appropriate molar ratios of M:Al are in the range from 1:10 to 1:10,000, preferably from 1:50 to 1:1000 and particularly preferably from 1:100 to 1:500.

The chosen complex of the formula I a or I b and the activator together form a catalyst system.

The activity of the catalyst system of the invention can be increased by addition of further aluminum alkyl of the formula $Al(R''')_3$ or aluminoxanes; aluminum alkyls of the formula $Al(R''')_3$ or aluminoxanes can also act as molar mass regulators. A further effective molar mass regulator is hydrogen. The molar mass can be regulated particularly effectively via the reaction temperature and the pressure. If a boron compound as described above is to be used, the addition of an aluminum alkyl of the formula $Al(R''')_3$ is particularly preferred.

Pressure and temperature conditions during the polymerization can be chosen within wide limits. Pressures in a range from 0.5 bar to 4000 bar have been found to be useful; preference is given to from 10 to 75 bar or high-pressure conditions of from 500 to 2500 bar. A suitable temperature range has been found to be from 0 to 120° C., preferably from 40 to 100° C. and particularly preferably from 50 to 85° C.

As monomers, mention may be made of the following olefins: ethylene, propylene, 1-butene, 1-pentene, 1-hexene, 1-octene, 1-decene and 1-undecene, with propylene and ethylene being preferred and ethylene being particularly preferred.

Suitable comonomers are α-olefins, for example from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

Solvents which have been found to be suitable are toluene, ortho-xylene, meta-xylene, para-xylene and ethylbenzene and also mixtures of these, also, under high-pressure conditions, supercritical ethylene.

The novel complex of the formula I a or I b can also be formed in situ in the polymerization reactor by mixing the deprotonated ligand II and the transition metal compound $MX_{y+1}$ in the polymerization reactor and, without isolating I a or I b, immediately activating the complex by means of one of the activators listed above. This method, too, also makes it possible to obtain the catalyst system of the present invention.

The catalyst systems of the present invention polymerize olefins to give polyolefins having a very high molecular weight.

Hydrogen has been found to be an effective chain transfer agent in polymerizations using the catalyst systems of the invention, i.e. the molecular weight of the polymers obtainable by means of the catalyst system of the present invention can be reduced by addition of hydrogen. If sufficient hydrogen is added, waxes are obtained. The hydrogen concentration required for this depends, inter alia, on the type of polymerization plant employed.

For the catalyst systems of the present invention to be able to be used in modern polymerization processes such as suspension processes, bulk polymerization processes or gas-phase processes, they have to be immobilized on a solid support. Otherwise, morphology problems with the polymer (lumps, deposits on walls, blockages in lines or heat exchangers) can occur and force shutdown of the plant. Such an immobilized complex will be referred to as a catalyst.

The catalyst systems of the present invention can be deposited on solid support materials. Suitable support materials are, for example, porous metal oxides of metals of groups 2 to 14 or mixtures thereof, also sheet silicates and zeolites. Preferred examples of metal oxides of groups 2 to 14 are $SiO_2$, $B_2O_3$, $Al_2O_3$, MgO, CaO and ZnO. Preferred sheet silicates are montmorillonites and bentonites; the preferred zeolite is MCM-41.

Particularly preferred support materials are spherical silica gels and aluminosilicate gels of the formula $SiO_2 \cdot a\, Al_2O_3$, where a is generally from 0 to 2, preferably from 0 to 0.5. Such silica gels are commercially available, e.g. silica gel SG 332, Sylopol® 948 or 952 or S 2101 from W. R. Grace or ES 70× from Crosfield.

As regards the particle size of the support material, mean particle diameters which have been found to be useful are from 1 to 300 µm, preferably from 20 to 80 µm, determined by known methods such as sieve methods. The pore volume of these supports is from 1.0 to 3.0 ml/g, preferably from 1.6 to 2.2 ml/g and particularly preferably from 1.7 to 1.9 ml/g. The BET surface area is from 200 to 750 m²/g, preferably from 250 to 400 m²/g.

To remove impurities, in particular moisture, adhering to the support material, the support materials can be baked before doping, with temperatures of from 45 to 1000° C. being suitable. Temperatures of from 100 to 750° C. are particularly useful for silica gels and other metal oxides. This baking can be carried out for from 0.5 to 24 hours, preferably from 1 to 12 hours. The pressure conditions depend on the process chosen; baking can be carried out in a fixed-bed process, a stirred vessel or else in a fluidized-bed process. Baking can in general be carried out at atmospheric pressure. However, reduced pressures of from 0.1 to 500 mbar are advantageous, a range from 1 to 100 mbar is particularly advantageous and a range from 2 to 20 mbar is very particularly advantageous. In the case of fluidized-bed processes, on the other hand, it is advisable to employ a slightly superatmospheric pressure in a range from 1.01 bar to 5 bar, preferably from 1.1 to 1.5 bar.

Chemical pretreatment of the support material with an alkyl compound such as an aluminum alkyl, a lithium alkyl or an aluminoxane is likewise possible.

It is also possible to form the novel complexes of the formula I a or I b in situ and deposit them on the solid support material and then to deposit the activator on the support material. If such a method of application to a support is chosen, the solid support material is preferably freed of traces of moisture by baking before doping is carried out.

In the case of a suspension polymerization process, use is made of suspension media in which the desired polymer is insoluble or soluble to only a slight extent, because otherwise deposits of product occur in the parts of the plant in which the product is separated off from the suspension medium and force repeated shutdowns and cleaning operations. Suitable suspension media are saturated hydrocarbons such as propane, n-butane, isobutane, n-pentane, isopentane, n-hexane, isohexane and cyclohexane, with isobutane being preferred.

Pressure and temperature conditions during the polymerization can be chosen within wide limits. A suitable pressure range has been found to be from 0.5 bar to 150 bar, preferably from 10 to 75 bar. A suitable temperature range has been found to be from 0 to 120° C., preferably from 40 to 100° C.

As monomers, mention may be made of the following olefins: ethylene, propylene, 1-butene, 1-pentene, 1-hexene, 1-octene, 1-decene and 1-undecene.

Suitable comonomers are α-olefins, for example from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

Furthermore, hydrogen has been found to be an effective chain transfer agent in polymerizations using the catalysts of the invention, i.e. the molecular weight of the polymers obtainable by means of the catalysts of the present invention can be reduced by addition of hydrogen. If sufficient hydrogen is added, waxes are obtained. The hydrogen concentration required for this depends, inter alia, on the type of polymerization plant employed. Addition of hydrogen increases the activity of the catalysts of the present invention.

The catalysts of the present invention can also be used together with one or more other polymerization catalysts known per se. Thus, they can be used together with Ziegler-Natta catalysts, supported metallocene catalysts containing transition metals of groups 4 to 6 of the Periodic Table of the Elements, catalysts based on late transition metals (WO 96/23010), Fe or Co complexes with pyridyldiimine ligands, as are disclosed in WO 98/27124 or chromium oxide catalysts of the Phillips type.

If a plurality of catalysts is used, it is possible to mix various catalysts with one another and to meter them in together or to use cosupported complexes on a common support or else to meter various catalysts separately into the polymerization vessel at the same point or at various points.

The following examples illustrate the invention.
General Preliminary Remarks:

All work was, unless indicated otherwise, carried out with exclusion of air and moisture using standard Schlenk techniques. Apparatus and chemicals were prepared accordingly. The polymer viscosity was determined in accordance with ISO 1628-3.

1. Preparation of the Ligands:

General procedure illustrated by way of example by that for ligand II.3

0.18 ml of diisopropylamine (1.3 nmol) was placed in a baked-out Schlenk tube which had been flushed with argon, dissolved in 10 ml of THF (absolute) and admixed at −80° C. with n-BuLi (0.72 ml, 1.1 equivalents, 2.0 M solution in pentane). After removing the cold bath (EtOH, $N_2$), the resulting LDA solution was stirred at room temperature for ½ hour.

Cyclohexylnitrile (0.144 g, 1.30 mmol) was added at −80° C. to the freshly prepared LDA solution. After removing the cold bath, the dissolved starting material was stirred for 2 hours at room temperature and thereby deprotonated (color change: yellowish to yellowish green).

0.24 g of benzophenone (1.3 mmol) was subsequently added at room temperature and the mixture was stirred overnight.

The yellow THF solution was then poured into 100 ml of ice water and extracted 3× with 25 ml each time of diethyl ether. The combined organic phases were washed with $H_2O$, dried over $Na_2SO_4$ and the organic solvents were separated off on a rotary evaporator. The yellow product crystallized out over a period of 2 hours. Subsequent recrystallization from ethyl acetate/hexane gave the pure β-hydroxynitrile.

Ligand II.1

The synthesis of this ligand was carried out by the literature method of E. Kaiser et al., J. Org. Chem. 1968, 33, 3403. The data agreed with the literature data.

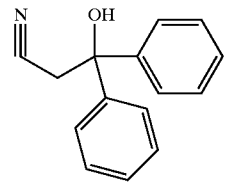

II.1

Ligand II.2

The synthesis of this ligand was carried out by the literature method of T. Cuvigny et al., J. Organomet. Chem. 1973, 57, C36–C38.

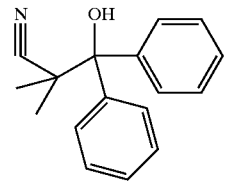

II.2

Ligand II.3

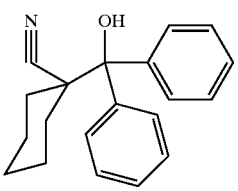

II.3

Yield 59%, empirical formula: $C_{20}H_{21}NO$, m.p.: 179–180° C.

1H NMR ($CDCl_3$): 1.11–1.17 (1H, m, $CH_2$), 1.61–1.79 (7H, m, $CH_2$), 2.04–2.08 (2H, m, $CH_2$), 2.67 (1H, s, OH), 7.29–7.67 (10H, m, phenyl)

13C NMR ($CDCl_3$): 22.8 ($CH_2$), 25.0 ($CH_2$), 30.8 ($CH_2$), 47.2 ($\underline{C}$—$(CH_2)_2$), 80.5 (C—OH), 123.1, 127.5, 127.7, 127.8, 143.1 (C-phenyl, CN)

IR (KBr, cm$^{-1}$): 3454 (s, broad), 3056 (w), 2966 (w), 2939 (w), 2921 (m), 2229 (m, CN), 1659 (w), 1600 (w), 1495 (m), 1445 (vs), 1355 (m), 1341 (m), 1279 (w), 1189 (m), 1165 (s), 1052 (vs), 870 (m), 749 (s), 702 (vs), 637 (m)

Ligand II.4

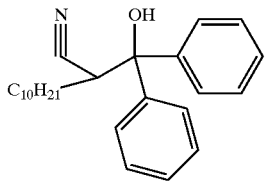

II.4

Yield: 60%, empirical formula: $C_{25}H_{33}NO$, color: white; m.p.: 66–67° C. (ethanol)

1H NMR (CDCl$_3$): 0.93 (3H, t, CH$_3$), 1.28–1.45 (17H, m, CH$_2$), 1.70–1.79 (2H, m), 3.02 (1H, s, C—OH), 7.26–7.58 (10H, m, phenyl)

$^{13}$C NMR (CDCl$_3$): 14.1 (CH$_3$), 22.6, 27.3, 27.6, 29.0, 29.2, 29.3, 29.4, 29.5, 31.8 (CH$_2$), 43.1 (CH), 78.6 (C—OH), 120.6, 125.7, 125.8, 127.5, 127.9, 128.4, 128.5, 143.0, 144.3 (C-phenyl, CN)

IR (KBr, cm$^{-1}$): 3355 (s, broad, OH), 3062 (w), 2952 (w), 2921 (m), 2871 (w), 2852 (m), 2263 (m, CN), 1495 (m), 1470 (m), 1449 (s), 1262 (m), 1177 (m), 1057 (s), 893 (m), 753 (s), 747 (s), 697 (vs)

MS: (LH$^+$–H$_2$O)=346.3 m/z, L=ligand

Ligand II.5

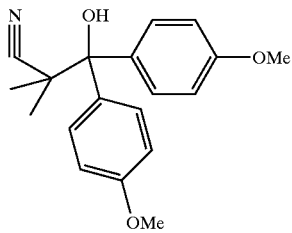

II.5

Yield: 72%, empirical formula: $C_{19}H_{21}NO_3$, color: white; m.p.: 104.5° C. (ethanol)

1H NMR (CDCl$_3$): 1.46 (6H, s, 2×CH$_3$), 2.88 (1H, s, OH), 3.90 (6H, s, 2×CH$_3$—O—), 6.86 (4H, d, phenyl (ligand)), 7.53 (4H, d, phenyl).

TABLE 1

Overview of the ligands of the formula II

| Complex | R$^1$ | R$^2$ | R$^3$ | R$^4$ | R$^5$ | Nu |
|---|---|---|---|---|---|---|
| II.1 | H | H | Ph | Ph | — | O |
| II.2 | Me | Me | Ph | Ph | — | O |
| II.3 | —(CH$_2$)5— | | Ph | Ph | — | O |
| II.4 | Me | Me | H | n-C$_{10}$H$_{21}$ | — | O |
| II.5 | Me | Me | p-An | p-An | — | O |
| II.6 | Me | Me | Ph | Ph | — | O |

Abbreviations: Me = CH$_3$, Ph = phenyl, p-An = para-anisyl = para-methoxyphenyl, —C$_2$H$_4$CN: β-cyanoethyl.

2. Synthesis of the Complexes

The ligand II.1 (517 mg, 2.32 mmol) was placed in a baked-out Schlenk tube which had been flushed with argon, dissolved in 20 ml of THF (absolute) and deprotonated at −80° C. on a cold bath (EtOH, N$_2$) by means of n-BuLi (1.2 ml, 2.4 mmol, 2.0 M in pentane). After removing the cold bath, the solution was stirred at room temperature for 1 hour (color change: yellow to light red).

After addition of the transition metal halide (ZrCl$_4$, 0.27 g, 1.12 mmol, 0.5 equivalent) at −80° C., the solution was allowed to warm and became dark red over a period of 1 hour. It was stirred for 18 hours.

The THF was subsequently distilled off in a high vacuum, and the orange or brown residue was suspended in toluene.

The LiCl formed in the reaction was removed from the suspension by filtration. The solution was subsequently evaporated to dryness in a high vacuum, and the residue was digested and washed 3× with 10 ml of hexane (absolute). The solvent was siphoned off and the pulverulent, orange complex I.b.1 was dried in a high vacuum.

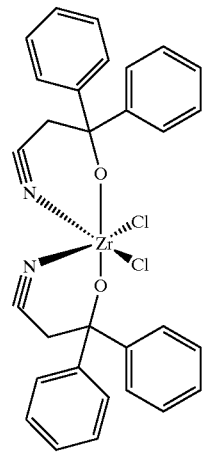

I.b.1

Yield: 75%, empirical formula: $C_{30}H_{24}Cl_2N_2O_2Zr$, color: brick red

1H NMR (CD$_2$Cl$_2$): 1.29 (4H, s, 2×CH$_2$), 7.09–7.49 (20H, m, aromatic)

Complex I.a.1

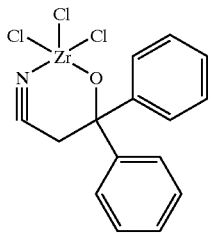

I.a.1

As a deviation from the general method, the residue after the THF had been distilled off was washed with CH$_2$Cl$_2$ and with hexane.

Yield: 61%, empirical formula: $C_{15}H_{12}Cl_3NOZr$, color: dirty orange

1H NMR (CD$_2$Cl$_2$): 1.87 (8H, s, 4×CH$_2$, 2 coordinated THF), 3.81 (8H, s, 4×CH$_2$—O, 2 coordinated THF), 4.54, 7.08–7.48 (10H, m, aromatic)

Complex I.a.2

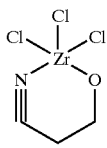

Yield: 69%, empirical formula: $C_3H_4Cl_3NOZr$, color: yellowish beige

1H NMR ($CD_2Cl_2$): 1.92 (2×$CH_2$, 1 coordinated THF, broad), 2.88 (broad), 3.79 (4H, 2×$CH_2$—O, 1 coordinated THF, broad), 4.50 (broad).

Complex I.a.3

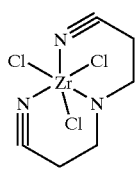

Yield: 70%, empirical formula: $C_6H_8Cl_3N_3Zr$, color: lemon yellow As a deviation from the general procedure, the complex was purified as follows: after the THF had been distilled off, the complex was suspended in $CH_2Cl_2$ and introduced onto a short Celite® column. It was subsequently eluted using 50 ml of acetonitrile.

Complex I.a.4

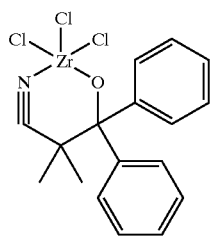

Yield: 81%, empirical formula: $C_{17}H_{16}Cl_3NOZr$, color: whitish yellow

1H-NMR ($CD_2Cl_2$): 1.64, 1.70 (6H, 2×$CH_3$), 1.87 (8H, s, 4×$CH_2$, 2 coordinated THF), 3.75 (4H, s, 4×$CH_2$—O, 2 coordinated THF), 7.28–7.72 (10H, m, aromatic)

Complex I.a.5

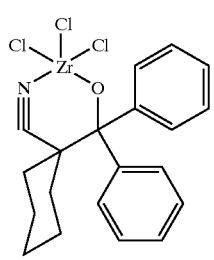

Yield: 73%, empirical formula: $C_{20}H_{20}Cl_3NOZr$, color: whitish yellow

1H-NMR ($CD_2Cl_2$): 0.86–1.88 (m, $CH_2$-ligand and $CH_2$ from coordinated THF molecules), 3.76, 4.45 (s, $CH_2$—O, coordinated THF molecules), 7.09–7.73 (m, phenyl)

13C NMR ($CD_2Cl_2$): 23.2, 23.5, 24.4, 24.9, 25.4, 25.8, 28.2, 48.6 ($\underline{C}$—($CH_2$)$_2$), 68.8 (O—$CH_2$, THF), 75.8, 76.4, 76.8 (C—O, isomers), 127.1, 127.2, 127.7, 127.9, 128.0, 128.2, 128.7, 129.3 (C-phenyl)

Complex I.a.6

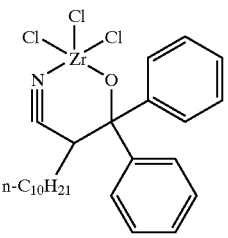

Yield: 81%, empirical formula: $C_{25}H_{32}Cl_3NOZr$, color: dirty yellow

1H-NMR ($CD_2Cl_2$): 0.84–0.88 (m, $CH_3$), 1.24 (s, $CH_2$), 1.84, 2.06 (8H, s, broad, 4×$CH_2$, 2 coordinated THF molecules), 3.72, 4.44 (8H, s, broad, 4×—O—$CH_2$, 2 coordinated THF molecules), 7.12–7.84 (10H, m, phenyl)

13C-NMR ($CD_2Cl_2$): 14.2 ($CH_3$), 23.0, 25.8, 27.9, 28.9, 29.5, 29.7, 29.8, 29.9, 32.2 ($CH_2$), 43.2, 44.2 (CH, 2 isomers), 75.7, 76.3 (C—O, 2 isomers), 126.4, 126.7, 126.9, 127.4, 127.5, 127.8, 128.2, 128.4, 128.5, 128.6, 128.8, 129.3, 129.6 (C-phenyl, 2 isomers)

Complex I.a.7

Yield: 62%, empirical formula: $C_{19}H_{20}Cl_3NO_3Zr$, color: yellow-orange

1H-NMR ($CD_2Cl_2$): 1.37 (3H, s, $CH_3$), 1.72 (3H, s, $CH_{13}$), 1.81 (s, 2×$CH_2$, coordinated THF), 3.65 (s, 2×$CH_2$—O, coordinated THF), 3.76, 3.87 (6H, 2×s, 2×$CH_3$—O), 6.81-7.83 (m, phenyl)

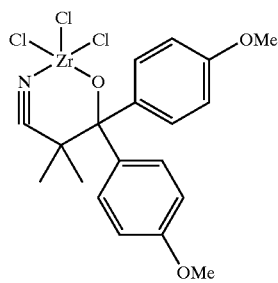

Complex I.b.2

As a deviation from the general method, the residue after the THF had been distilled off was washed with $CH_2Cl_2$ and with hexane.

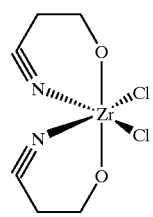

Yield: 53%, empirical formula: $C_6H_8Cl_2N_2O_2Zr$, color: light yellow

1H-NMR ($CD_2Cl_2$): 1.81 (m, CH2, coordinated THF), 2.57 (t, $CH_2$), 3.67 (m, $CH_2$—O, coordinated THF), 3.84 (m,

CH$_2$—O)

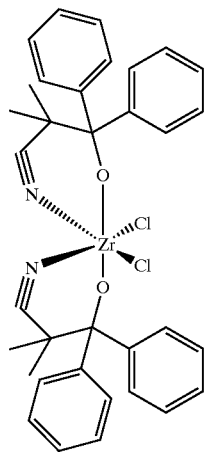

Complex I.b.3

Yield: 76%, empirical formula: C$_{34}$H$_{32}$Cl$_2$N$_2$O$_2$Zr, color: white

1H NMR (CD$_2$Cl$_2$): 1.27, 1.48 (12H, 4×CH$_3$), 1.79 (4H, s, 2×CH$_2$, 1 coordinated THF), 3.72 (4H, s, 2×CH$_2$—O, 1 coordinated THF), 7.21–7.80 (20H, m, aromatic)

TABLE 2

Overview of the complexes of the formulae I a and I b

| Complex | R$^1$ | R$^2$ | R$^3$ | R$^4$ | R$^5$ | M | X | Nu |
|---|---|---|---|---|---|---|---|---|
| I.a.1 | H | H | Ph | Ph | — | Zr | Cl | O |
| I.a.2 | H | H | H | H | — | Zr | Cl | O |
| I.a.3 | H | H | H | H | —C$_2$H$_4$CN | Zr | Cl | N |
| I.a.4 | Me | Me | Ph | Ph | — | Zr | Cl | O |
| I.a.5 | —(CH$_2$)$_5$— | | Ph | Ph | — | Zr | Cl | O |
| I.a.6 | H | n-C$_{10}$H$_{21}$ | Ph | Ph | — | Zr | Cl | N |
| I.a.7 | Me | Me | p-An | p-An | — | Zr | Cl | O |

TABLE 2-continued

Overview of the complexes of the formulae I a and I b

| Complex | R$^1$ | R$^2$ | R$^3$ | R$^4$ | R$^5$ | M | X | Nu |
|---|---|---|---|---|---|---|---|---|
| I.b.1 | H | H | Ph | Ph | — | Zr | Cl | O |
| I.b.2 | H | H | H | H | — | Zr | Cl | O |
| I.b.3 | Me | Me | Ph | Ph | — | Zr | Cl | O |

Abbreviations: Me = CH$_3$, Ph = phenyl, —C$_2$H$_4$CN: β-cyanoethyl, p-An: para-anisyl.

3. Polymerization Experiments 3.1. Polymerization at Atmospheric Pressure

In a Schlenk tube which had been made inert, a solution composed of 20 mg of the complex to be examined, 1 ml of 30% strength by weight MAO solution (in toluene) and 50 ml of toluene was prepared. This reaction mixture was, unless indicated otherwise, stirred under an ethylene atmosphere for 90 minutes at room temperature. The precipitated white solid was filtered off, the solid was washed with methanol and dried under reduced pressure. The polymer was obtained in the form of a white powder.

3.2. Polymerization in an Autoclave 20 mg of the complex to be examined, 2 ml of 30% strength by weight MAO solution in toluene and 400 ml of toluene were placed in a 1 l steel autoclave which had been made inert. At 70° C., the autoclave was pressurized with ethylene to a pressure of 40 bar. This pressure was kept constant during the 90 minute duration of the experiment by introduction of further ethylene. The reaction was stopped by venting and the polymer was isolated by filtration, subsequent washing with methanol and drying under reduced pressure.

3.3. Copolymerization of Ethylene/Hexene

The procedure of 3.2 was repeated, but 20 ml of 1-hexene were placed in the autoclave at the beginning together with the other reagents.

3.4. Polymerization Using Hydrogen as Molar Mass Regulator

The procedure of 3.2. is repeated, but 4 l of hydrogen (at STP) are introduced into the autoclave at the beginning.

The results are summarized in Table 3.

TABLE 3

Polymerization results

| | Polymerization of ethylene at atmospheric pressure | | Polymerization of ethylene at 40 bar | | Copolymerization of ethylene/hexene | | | Influence of hydrogen on the polymerization of ethylene | |
|---|---|---|---|---|---|---|---|---|---|
| Complex | Yield [g] | η value [dl/g] | Yield [g] | η value [dl/g] | Yield [g] | η value [dl/g] | Hexene content of copolymer [% by weight] | Yield [g] | η value [dl/g] |
| I.a.1 | 1.4 | 28.5 | 48.0 | 45.5 | 27.5 | 34.9 | <0.8 | 23.5 | 24.1 |
| I.b.1 | 0.2 | 18.5 | | | | | | | |
| I.a.2 | 0.1* | 17.0 | | | | | | | |
| I.a.3 | 0.1* | 17.0 | | | | | | | |
| I.a.4 | 2.4 | 12.2 | 45.7 | 28.0 | 21.5 | 9.9 | <0.8 | 10.4 | 10.9 |
| I.a.5 | 3.4 | | | | | | | | |
| I.b.2 | 0.1** | 11.8 | | | | | | | |
| I.b.3 | 1.0 | 14.6 | 20.0 | 9.8 | 9.7 | 12.2 | <0.8 | 11.4 | 9.6 |

*Polymerization time of 180 minutes,
**polymerization time of 120 minutes

We claim:
1. A complex of the formula I a or I b,

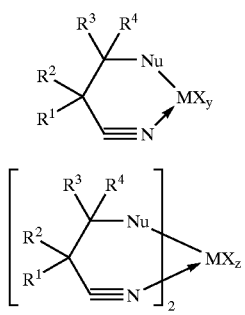

where the variables are defined as follows:
M is selected from the group consisting of Ti, Zr, Hf, V, Nb and Ta;
y corresponds to the oxidation state of M minus 1;
z corresponds to the oxidation state of M minus 2;
Nu is selected from the group consisting of O, S and N—$R^5$;
X are identical or different and are selected from the group consisting of a halogen, a $C_1$–$C_8$-alkyl, a $C_3$–$C_{12}$-cycloalkyl, a $C_7$–$C_{13}$-aralkyl) and a $C_6$–$C_{14}$-aryl,
$R^1$ to $R^5$ are identical or different and are selected from the group consisting of
a hydrogen,
a substituted $C_1$–$C_{18}$-alkyl, an unsubstituted $C_1$–$C_{18}$-alkyl,
a substituted $C_2$–$C_{18}$-alkenyl having from one to 4 isolated or conjugated double bonds, an unsubstituted $C_2$–$C_{18}$-alkyl, having from one to 4 isolated or conjugated double bonds,
a substituted $C_3$–$C_{12}$-cycloalkyl, an unsubstituted, $C_3$–$C_{12}$-cycloalkyl,
a $C_7$–$C_{13}$-aralkyl,
an unsubstituted $C_6$–$C_{14}$-aryl, a substituted $C_6$–$C_{14}$-alkyl, wherein the substituted $C_6$–$C_{14}$-alkyl has one or more identical or different substituents selected from the group consisting of
a substituted $C_1$–$C_{18}$-alkyl, an unsubstituted $C_1$–$C_{18}$-alkyl,
a substituted $C_1$–$C_{18}$-alkenyl, an unsubstituted $C_1$–$C_{18}$-alkenyl,
a $C_3$–$C_{12}$-cycloalkyl,
a $C_7$–$C_{13}$-aralkyl,
a $C_6$–$C_{14}$-aryl,
a halogen,
a substituted $C_1$–$C_6$-alkoxy, an unsubstituted $C_1$–$C_6$-alkoxy,
a $C_6$–$C_{14}$-aryloxy,
a $SiR^6R^7R^8$ and an O—$SiR^6R^7R^8$;
an unsubstituted five- member nitrogen-containing heteroaryl radical, a substituted five-member nitrogen-containing hetereoaryl radical, an unsubstituted six-membered nitrogen-containing heteroaryl radical wherein one or more substituents are identical or different and are selected from the group consisting of
a substituted $C_1$–$C_{18}$-alkyl, an unsubstituted $C_1$–$C_{18}$-alkyl,
a substituted $C_2$–$C_{18}$-alkenyl, an unsubstituted $C_2$–$C_{18}$-alkenyl,
a $C_3$–$C_{12}$-cycloalkyl,
a $C_7$–$C_{13}$-aralkyl,
a $C_6$–$C_{14}$-aryl,
a halogen,
a $C_1$–$C_6$-alkoxy,
a $C_6$–$C_{14}$-aryloxy,
a $SiR^6R^7R^8$, and an O—$SiR^6R^7R^8$;
where adjacent radicals $R^1$ to $R^4$ may be joined to one another to form a 5-membered to 12-membered ring which may in turn bear substituents selected from the group consisting of a substituted $C_1$–$C_8$-alkyl, an unsubstituted $C_1$–$C_8$-alkyl, a substituted $C_2$–$C_8$-alkenyl having from one to 4 isolated or conjugated double bonds an unsubstituted $C_2$–$C_8$-alkenyl having from one to 4 isolated or conjugated double bonds, a substituted $C_3$–$C_{12}$-cycloalkyl, an unsubstituted $C_3$–$C_{12}$-cycloalkyl, a $C_7$–$C_{13}$-aralkyl, and a $C_6$–$C_{14}$-aryl;
wherein $R^6$ to $R^8$ are identical or different and are selected from the group consisting of a hydrogen, a $C_1$–$C_8$-alkyl, a $C_3$–$C_{12}$-cycloalkyl, a $C_7$–$C_{13}$-aralkyl, and a $C_6$–$C_{14}$-aryl.

2. A complex as claimed in claim 1, wherein Nu is oxygen, M is selected from the group consisting of Ti and Zr, X is halogen and at least one radical $R^1$ to $R^4$ is different from hydrogen.

3. A process for the polymerization or copolymerization of olefins, comprising:
contacting one or more complexes of the formula I a or I b as claimed in claim 1 with an olefin.

4. A process for preparing a complex as claimed in claim 1, which comprises:
deprotonating a ligand of the formula II

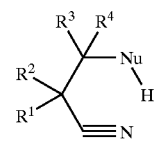

by means of a base and subsequently
reacting the product with a metal compound $MX_{y+1}$, where M is selected from the group consisting Ti, Zr, Hf, and V, and X is selected from the group consisting of a halogen, a $C_1$–$C_8$-alkyl, a $C_3$–$C_{12}$-cycloalkyl, a $C_7$–$C_{13}$-aralkyl, and a $C_6$–$C_{14}$-aryl, where $MX_{y+1}$ may optionally be stabilized by additional uncharged ligands.

5. A process for preparing a supported catalyst for the polymerization or copolymerization of olefins, which comprises depositing one or more complexes as claimed in claim 1 and optionally an activator on a solid support.

6. A supported catalyst for the polymerization or copolymerization of olefins which is obtained by a process as claimed in claim 5.

7. A process for the polymerization or copolymerization of olefins, comprising:
contacting a supported catalyst as claimed in claim 6 with an olefin.

8. A process for the polymerization or copolymerization of olefins as claimed in claim 3, further comprising:
contacting one or more complexes of the formula I a or I b with an activator.

9. A process for the ploymerization or copolymerization of olefins, which comprises:

contacting one or more complexes of the formula I a or I b as claimed in claim 2 with an olefin.

10. A process for the polymerization or copolymerization of olefins as claimed in claim 9, further comprising:

contacting one or more complexes of the formula I a or I b with an activator.

11. A process for preparing a complex as claimed in claim 2, which comprises firstly deportonating a ligand of the formula II

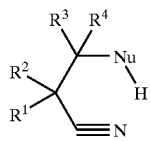

by means of a base and subsequently reacting the product with a metal compound $MX_{y+1}$, where M is selected from the group consisting of Ti, Zr, Hf, V, and X is selected from the group consisting of a halogen, a $C_1$–$C_8$-alkyl, a $C_3$–$C_{12}$-cycloalkyl, a $C_7$–$C_{13}$-aralkyl, and a $C_6$–$C_{14}$-aryl, where $MX_{y+1}$ may optionally be stabilized by additional uncharge ligands.

12. A process for preparing a supported catalyst for the ploymerization or copolymerization of olefins, which comprises depositing one or more complexes as claimed in claim 2 and optionally an activator on a solid support.

13. A process for polymerization or copolymerization of olefins, which comprises:

contacting the supported catalysts of claim 12 with an olefin.

* * * * *